United States Patent [19]

Kozak et al.

[11] Patent Number: 5,066,295
[45] Date of Patent: Nov. 19, 1991

[54] ROTATABLE SURGICAL SNARE

[75] Inventors: Mark Kozak, Euclid; Michael Nichols, Mentor, both of Ohio

[73] Assignee: Mill-Rose Laboratories, Inc., Mentor, Ohio

[21] Appl. No.: 862,683

[22] Filed: May 13, 1986

[51] Int. Cl.[5] .............................................. A61B 17/36
[52] U.S. Cl. ..................................................... 606/47
[58] Field of Search ........................................ 128/4–8,
128/303.1, 303.13–303.17, 751, 755, 309,
321–324; 403/DIG. 4, 315, 319, 325, 341, 348,
349, 353

[56] References Cited

U.S. PATENT DOCUMENTS

| 1,130,726 | 3/1915 | Greve | 403/348 |
| 1,199,690 | 9/1916 | Gillan | 403/348 |
| 2,484,059 | 10/1949 | Wallace | 128/303.15 |
| 3,805,791 | 4/1974 | Serberth et al. | 128/303.14 |
| 3,828,790 | 8/1974 | Curtiss et al. | 128/303.14 |
| 3,955,578 | 5/1976 | Chamness et al. | 128/303.15 |
| 4,326,530 | 4/1982 | Fleury | 128/303.14 |
| 4,362,414 | 12/1982 | Volz | 403/349 |
| 4,592,341 | 6/1986 | Omagari et al. | 128/4 |
| 4,598,699 | 6/1986 | Garren et al. | 128/4 |

OTHER PUBLICATIONS

Hobbs Medical Inc. advertisement May 1985 (prior to).
Microvasive advertisement May 1985 (prior to).
Olympus advertisement May 1985 (prior to).
American Endoscopy Inc. advertisement May 1985 (prior to).

Primary Examiner—Max Hindenburg
Attorney, Agent, or Firm—Watts, Hoffmann, Fisher & Heinke

[57] ABSTRACT

The invention provides an improved surgical snare having an operating cable freely rotatable while the handle is maintained steady, having a rotating assembly mounted in the handle so that the axis of rotation of the assembly is essentially coaxial with the longitudinal axis of the handle and having a quick disconnect-connect means for attaching the operating cable to the rotating assembly without external clamping means.

15 Claims, 3 Drawing Sheets

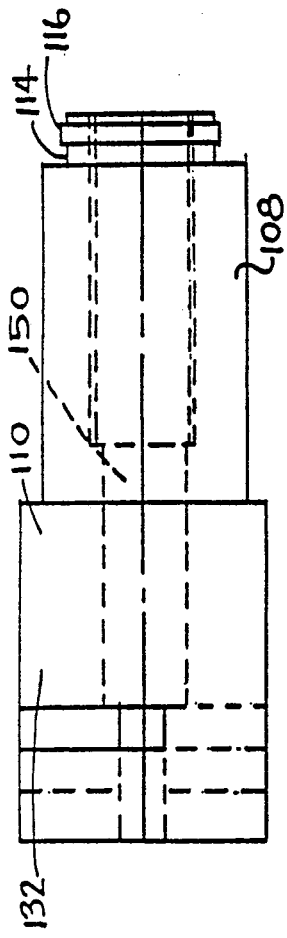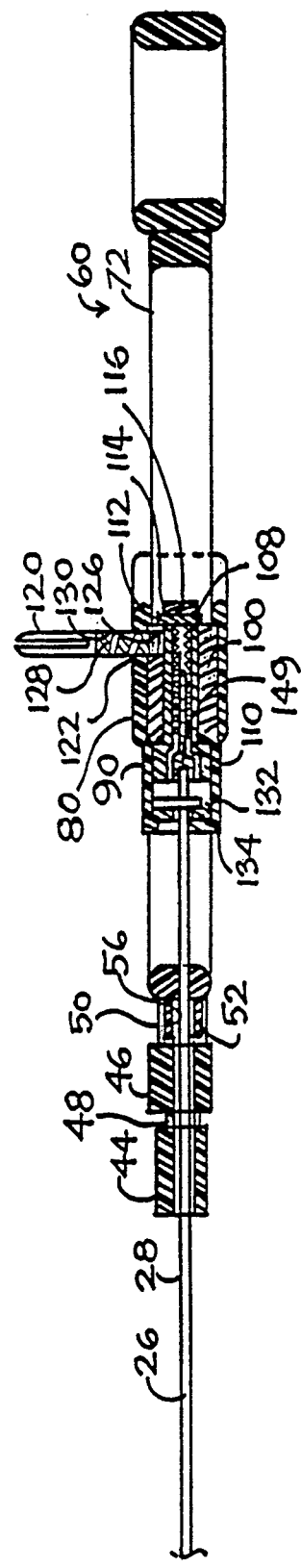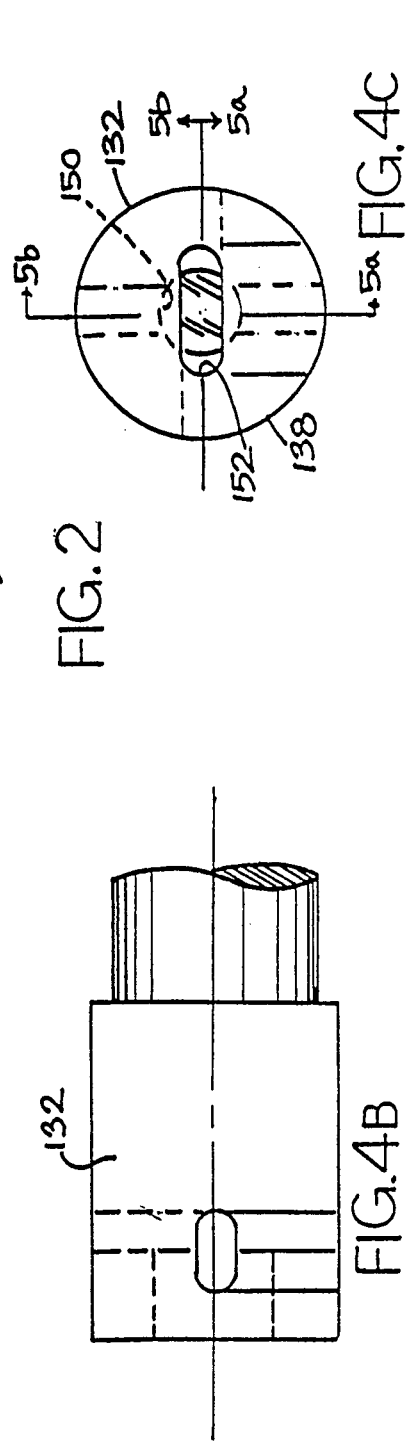

ROTATABLE SURGICAL SNARE

TECHNICAL FIELD

This invention relates generally to surgical snares and, more particularly, to an improved rotatable surgical snare for endoscopic polypectomy use.

BACKGROUND ART

Polypectomes for surgically removing colonic polyps usually comprise an electrocautery snare retractable into a long flexible sheath by means of an electrically conducting cable and a handle connected to the sheath and operating cable for retracting and protracting the snare and for connection to a source of electric power.

In use, the polypectome with the snare retracted is positioned near a polyp with the aid of an endoscope. Once the polyp is located, the operator employes the handle to protract the snare to its open position. The snare, however, rarely protracts from the sheath ideally positioned to engage the polyp; the operator must manipulate the entire handle in order to rotate the snare. Since the handle has an electrical connection, it is not uncommon for the connection to become entangled around the operator's hand and impede the procedure. Such a snare is shown in U.S Pat. No. 3,828,790.

This drawback can be obviated by providing a snare which is rotatable while the handle is held stationary in the operator's hand. A surgical snare having an operating cable rotatable in a sheath by means of a rotating assembly mounted above a snare handle is shown in U.S. Pat. No. 3,955,578. While the handle-mounted rotating assembly overcomes a problem of the need to manipulate the entire instrument in order to position the snare, its location away from the main axis of the handle makes it difficult to hold the handle stationary while rotation is effected The problem associated with a rotating assembly mounted away from the longitudinal axis of the handle are increased for operators with small hands.

In both U.S. Pat. No. 3,838,790 and 3,995,578 the operating cable is attached to the handle by external clamping means, such as a clamping knob threaded onto the handle or a set screw threaded into the handle. Knobs and set screws not convenient, are sometimes difficult to use or loosen in use, and are easily lost during the assembly and disassembly of the instrument necessary for cleaning or to replace damaged or bent snares.

DISCLOSURE OF THE INVENTION

The invention provides an improved surgical snare having an operating cable freely rotatable while the handle is maintained steady, having a rotating assembly mounted in the handle so that the axis of rotation of the assembly is essentially coaxial with the longitudinal axis of the handle and having a quick disconnect-connect means for attaching the operating cable to the rotating assembly without external clamping means More particularly, the invention provides, in an endoscopic snare having a sheath, an electrically conducting cable with a snare at a distal end movable into and out of the sheath, and a manual operating assembly attached to the sheath and to a proximal end of the cable, the improvement in the manual operating assembly of an elongated holder having a body portion and a cable actuator wherein the body portion has a central longitudinal recess that opens through two opposite sides to define a pair of parallel guides upon which the actuator is mounted; the actuator has an electrically conducting, snare-rotating member that is slidable between the parallel guides; the snare-rotating member and the proximal end of the cable each have means cooperating to form a quick disconnect connection; and the holder, the snare-rotating shaft and the cable are constructed and arranged to have a common longitudinal axis.

The body portion is rectangular is cross-section and the central longitudinal recess opens through the two wider sides of the rectangle. The cable actuator has a transverse rectangular recess for slidably receiving the rectangular body.

The electrically conducting, snare-rotating member comprises a block with a bore The block is located within the recess of the actuator and retained against rotation by the transverse shape of the recess in the actuator. A finger operable rotary member is journaled in the bore. An enlarged cylindrical portion with a plastic sleeve extends from the block and beyond the distal face of the actuator It fits within the parallel guides and protrudes from opposite sides of the central longitudinal recess of the body so that it is easily gripped and turned with the operator's fingers.

Means are provided communicating through the actuator and the block to connect the block to the actuator and to make sliding electrical contact with the rotatably held shaft. This means preferably comprises a contact post passing through an aperture in the actuator and threadedly received in a corresponding aperture in the block. The aperture in the block intersects the central bore of the block so that a spring retained within the contact post makes sliding contact with the rotatably held cylindrical shaft.

Means are provided on both the proximal end of the cable and in the extending portion of the snare-rotating member that cooperate to form a quick-disconnect connection. The proximal end of the cable has a small transverse rod at the end of the cable and the snare-rotating member has an elongated aperture in its distal face that forms a passage into a central recess that has a transverse stop and a spring biased detent, all of which allow the proximal end of the cable to be inserted and releasably engaged in the snare-rotating member.

The proximal end of the body has a thumb ring and each one of the lateral sides of the actuator has a finger ring. The thumb and finger rings are coplanar with each other, with the holder, and with the electrically conducting, snare-rotating member.

The improved rotatable snare provides the advantage of a compact, easily handled instrument. The location of the snare turning knob within the parallel guides upon which the cable actuator slides back and forth to protract and retract the cable ensures facile manipulability by all operators regardless of hand size. Also, the construction of the snare-rotating member, while compact, provides an effective mechanical and electrical interconnection with the snare that avoids the need for tools or screws in connecting or disconnecting the snare and facilitates easy removal of the rotating member from the actuator.

Other advantages and a more complete understanding of the invention will be had from the following detailed description when taken in conjunction with the accompanying drawings.

BRIEF DESCRIPTION OF DRAWINGS

FIG. 2 is a longitudinal sectioned view of the surgical snare of FIG. 1 taken along the line 2—2;

FIG. 3 is a side elevational view of the quick disconnect-connect mechanism in the proximal end of the cable;

FIGS. 4a and 4b are side elevational views of the snare-rotating member;

FIG. 4c is an end elevational view taken from the left end of FIG. 4a;

FIGS. 5a and 5b are pre-shaped sections of one longitudinal half of the snare-rotating member taken along the lines 5a—5a and 5b—5b, respectively, of FIG. 4a; and FIG. 6 is a partial longitudinal sectional view of the snare-rotating member taken along the line 5a—5b of FIG. 4a.

BEST MODE FOR CARRYING OUT THE INVENTION

Figure 1:
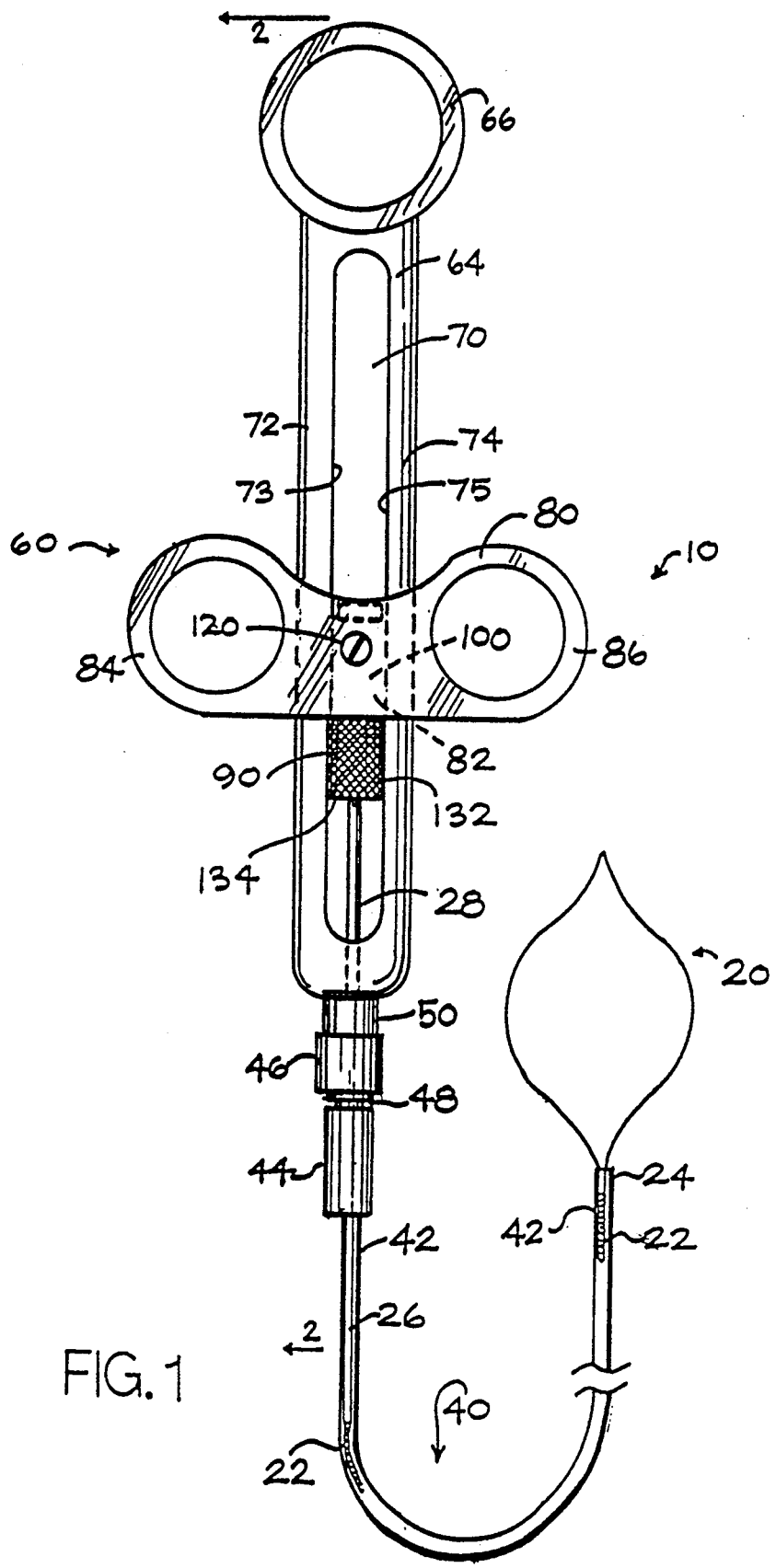
FIG. 1 is a top plan view of the rotatable surgical snare of the present invention.

Refering to FIG. 1, the improved rotatable snare instrument of the present invention is designated generally as 10 and comprises a surgical snare 20, a flexible portion 40 and a manual operating assembly 60.

As shown in FIG. 1, the snare 20 is in its protracted position and is connected to the distal end of an electrically conductive flexible operating cable 22 by means of a crimped-on collar 24. The conductive flexible operating cable 22 has a proximal stiffened rod-like portion 26 to facilitate connection to the manual operating assembly 60. The rod-like portion 26 is covered with a non-conductive material jacket 28. The operating cable 22 is contained within a non-conductive flexible sheath 42 open at the distal end to allow retraction and protraction of the snare 20. The sheath 42 has a threaded coupler 44 at the proximal end for attachment to a second coupler 46 for mounting the flexible portion 40 to the manual operating assembly 60. The second coupler 46 has a threaded portion 48 for attachment to the coupler 44 and a luer-lock like portion 50 for attachment to a corresponding luer-lock like portion 52 on the operating assembly 60. As best seen in FIG. 2, the luer-lock like portion 52 defines a passage 56 for receiving the stiffened rod-like portion 26 of the cable 22. Alternatively, the connection between the sheath 42 and the manual operating assembly 60 may be one-piece, but assembly and disassembly of the instrument—which can be 1.5 m long—is facilitated by the coupler arrangement as shown in FIG. 1.

The manual operating assembly 60 has an elongated generally rectangular body 64 with a thumb ring 66 at the proximal end. The body 64 has a central longitudinal recess 70 that opens through the two wider sides of the rectangle, resulting in a pair of elongated guide bars 72, 74. The inwardly facing surfaces 73, 75 are cylindrically curved. A cable actuator 80, having a generally rectangular transverse through-passage 82 for receiving the elongated body 64, is slidable on the guide bars 72, 74, by means of a pair of finger rings 84, 86 located on opposite lateral sides of the actuator and in the same plane as the thumb ring 66. The through-passage 82 of the actuator 80 engages an electrical-torque transmitting member 90 that is located between the interior surfaces 73, 75 of the guide bars 72, 74.

The electrical-torque transmitting member 90 has an electrically conductive block 100 secured to the actuator and in which a first reduced diameter portion 108 of a cylindrical snare-rotating shaft 110 is journaled. As best seen in FIG. 2, the cylindrical snare-rotating shaft 110 is retained in the electrically conducting block 100 for relative rotation by means of a resilient retaining ring 112 received in a channel 114 in a second reduced diameter portion 116 of the cylindrical snare-rotating shaft 110. The block 100 is constructed to fit within the actuator 80 without protruding beyond it into the recess 70. The block 100 is retained against rotation within the actuator 80 by the transverse shape of the through passage 82 and retained within the actuator 80 by means of a contact post 120 that passes through a first aperture 122 in the actuator 80 and that is threadedly received in a second corresponding aperture 126 in the block 100. Electrical contact between the contact post 120 and the snare-rotating shaft 110 is established by means of a spring 128 contained within a recess 130 at one end of the contact post 120. The spring 128 is in sliding contact with the reduced diameter portion 108 of the snare-rotating shaft 110 received within the block 100.

As seen in FIG. 2, the cylindrical snare-rotating shaft 110 has a distally facing expanded diameter knob portion 132 extending beyond the distal face of the actuator 80. The knob 132 has a diameter larger than the width of the narrow sides of the rectangular body 64 of the manual operating assembly 60 and is constructed so as to nest within the cylindrical interior surfaces 73, 75 of the guide bars 72, 74. The knob 132 protrudes from the central longitudinal recess 70 of the rectangular body 74, so that it is easily gripped by the operator's fingers for manual rotation. The knob 132 is covered with a non-conducting material 134 and may be knurled to facilitate gripping and rotation.

The distal end of the operating cable 22 and the snare-rotating shaft 110 each have means cooperating to form a quick-disconnect connection that locates the axis of rotation of the cable 22, the shaft 110, and the manual operating assembly 60 along a common line. As shown in FIG. 3, the distal end of the rod-like portion 26 of the cable 22 has a generally cylindrical push portion 140 and a generally cylindrical locking portion 142 normal to and interposed between the push portion 140 and the rod-like portion 26 of the cable 22.

As best seen in FIGS. 4a, 4b, 4c, 5a, 5b, and 6 the snare-rotating shaft 110 is constructed so that a member 149 in the interior of the shaft 110 acts as a spring biased detent to hold the locking portion 142 of the cable 22. The shaft 110 has a centrally located circular longitudinal recess 150 passing through the first and second reduced diameter portions 108, 116 and into the knob portion 132 where it terminates at the distally facing end 138 of the knob portion 132 in a elliptically shaped, centrally located recess 152. The elliptical recess 152 is dimensioned to receive the generally cylindrical locking portion 142 of the rod-like portion 26 of the cable 22.

Figure 5B:
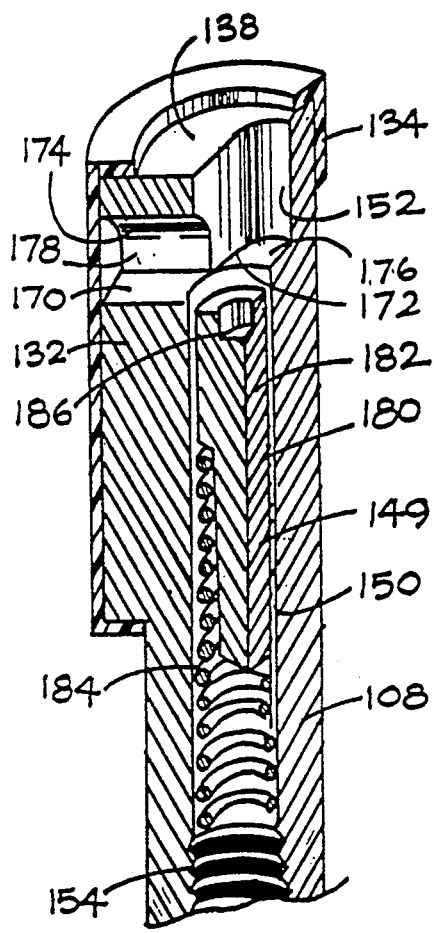
Figure 5A:
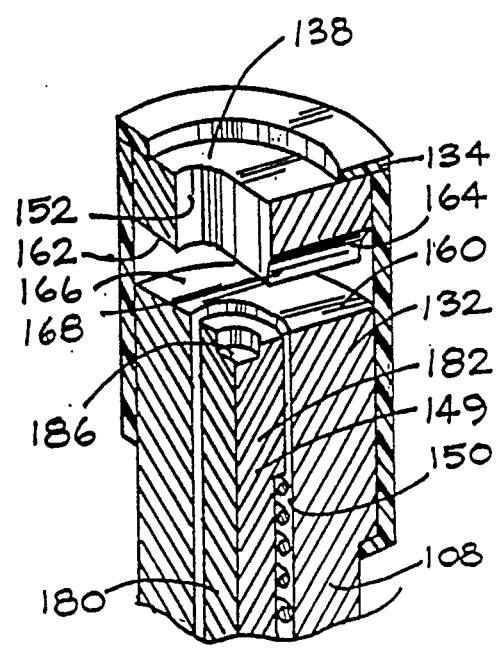
Figure 6:
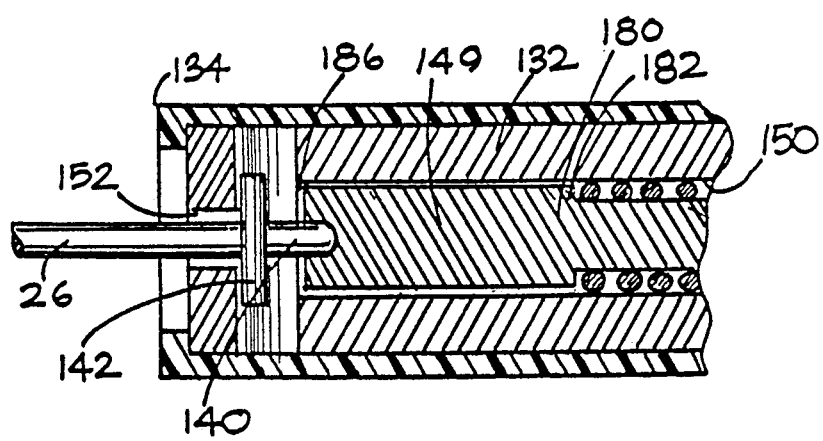

Two slots 160, 170 transverse to the elliptical recess 152 and 180° apart are located in the knob 132. The slots 160, 170 extend from the exterior of the knob 132 to intersect the elliptical recess 152. As shown in FIGS. 5a and 5b, the slots 160, 170 communicate with the elliptical recess 152 and, in the orientation shown in FIGS. 5a and 5b, have a low ceiling portion 162, 172 near the long axis of the cylindrical recess 152 and a high ceiling portion 164, 174 near the short axis of the cylindrical recess. The intersection of the circular recess 150, the elliptical recess 152 and the low ceiling portions 162, 172 of the slots 160, 170 define two locking-portion sliding-surfaces 166, 176. The radial sides of the high ceiling portions 164, 174 define locking-portion stop-surfaces 168, 178.

A spring biased circular elongated plunger 180 is located within the circular recess 150. The plunger 180 has an enlarged head 182 to retain a spring 184 within the circular recess 150 proximally of the head 182. The plunger 180 and spring 184 are retained within the circular recess 150 by means of a threaded fastener screwed into a threaded proximally facing portion 154 in the circular recess 150. The head 182 has a centrally located distally facing dimple 186 dimensioned so as to receive the push portion 140 of the cable 22.

To assemble the instrument, the transverse rod on the end of the cable is inserted into the elliptical opening in the knob and rotated 90°. A spring-biased detent retains the rod in the internal grooves of the knobs. More particularly, the distal end of the cable 22 is passed through the passage 56 in the luer-like portion 52 of the manual operating assembly 60. The cylindrical locking portion 142 of the cable 22 is inserted through the elliptical recess 152 in the knob 132. Pressure is applied during insertion so that the cylindrical locking portion 142 contacts the locking portion sliding surfaces 166, 170 and the push portion 142 engages the dimple 186 to depress the plunger 180. Reorientation through rotation by about 90° of the cylindrical locking portion 142 along the sliding surfaces 166, 176 causes the locking portion 142 to slide from the low ceiling portions 162, 172 to the high ceiling portions 164, 174 until reorientation is completed by the locking portion 142 encountering stopping surfaces 168, 178. Releasing the pressure on the cable allows the plunger 180 to hold the locking portion 142 securely in the high ceiling portions 164, 174. Removal of the cable 22 from the snare-rotating shaft 110 is effected by applying pressure to the cable 22 to depress the plunger 180, rotating the locking portion 142 out of the high and low ceiling portions 164, 174, 162, 172 and withdrawing it from the elliptical recess 152.

Variations and modifications of the invention will be apparent to those skilled in the art from the above detailed description Therefore, it is to be understood that, within the scope of the appended claims, the invention can be practiced otherwise than as specifically shown and described.

We claim:

1. In an endoscopic snare having a sheath, an electrically conducting cable with a snare at a distal end movable into and out of the sheath and a manual operating assembly attached to the sheath and to a proximal end of the cable, the improvement wherein the manual operating assembly comprises an elongated holder having a body portion, and a cable actuator, said body portion having a central longitudinal recess open through two opposite sides to define a pair of parallel guides upon which the actuator is slidably mounted, said pair of parallel guides each having an interiorly facing arcuate surface, said cable actuator having an electrically conducting snare-rotating member between said parallel guides, said snare-rotating member partially encircled by the interiorly facing arcuate surfaces of said parallel guides, said snare-rotating member and the proximal end of the cable each having means cooperating to form a quick disconnect connection wholly within said snare-rotating member, and said elongated holder, snare-rotating member and cable being constructed and arranged to have a common longitudinal axis.

2. The endoscopic snare as claimed in claim 1 wherein the body portion is rectangular in cross-section and wherein the central longitudinal recess opens through the two wider opposite sides of the rectangular body.

3. The endoscopic snare as claimed in claim 2 wherein the cable actuator has a transverse rectangular recess for slidably receiving the body portion of the manual operating assembly.

4. The endoscopic snare as claimed in claim 3 wherein the electrically conducting snare-rotating member comprises a block having a bore located within and retained against rotation by the rectangular recess of the cable actuator, and a cylindrical shaft rotatably held within the bore of the block.

5. The endoscopic snare as claimed in claim 4 wherein the cylindrical shaft has a cylindrical knob extending beyond a distal face of the actuator and having a diameter so as to protrude from opposite sides of the central longitudinal recess in the two wider opposite sides of the rectangular body.

6. The endoscopic snare as claimed in claim 4 wherein the actuator and the block have means communicating there through to connect the block to the actuator and to make sliding electric contact with the rotably held cylindrical shaft.

7. The endoscopic snare as claimed in claim 6 wherein the means connecting the block to the actuator and making contact with the shaft comprises a contact post received through a first recess in the actuator and threadly received in a second recess in the block, and a spring retained within the contact post extending out of the post and in sliding contact with the shaft.

8. The endoscopic snare as claimed in claim 1 wherein the means cooperating to form the quick-disconnect connection comprises a cylindrical transverse rod located near the proximal end of the cable and further comprises an elliptical recess transversely centrally located in a distal face of the snare-rotating member, said recess communicating with at least one locking groove, and a spring biased member retained in the shaft of the snare-rotating member and located to releasably engage the rod in the groove.

9. The endoscopic snare as claimed in claim 1 wherein the proximal end of the body has a thumb ring and each one of the lateral sides of the actuator has a finger ring, said thumb ring and finger rings being coplanar with each other, with the elongated holder, and with the electrically conducting snare-rotating member.

10. In a endoscopic snare having a sheath, an electrically conducting cable with a snare at a distal end movable into and out of the sheath and a manual operating assembly attached to the sheath and to a proximal end of the cable, the improvement wherein the manual operating assembly comprises an elongated holder having a rectangular body portion, a thumb ring, and a cable actuator, said body portion having a central longitudinal recess open through the two wider opposite sides of the rectangular body to define a pair of parallel guides upon which the actuator is slidably mounted, said parallel guides having cylindrically curved interior surfaces, said actuator having a finger ring on each one of two lateral sides and a transverse rectangular recess, an electrically conducting snare-rotating member located with said actuator, said snare-rotating member comprising a block journaled to receive a snare rotating shaft attached for relative rotation, said block and shaft slidable between said curved interior surfaces by means of said actuator, said block retained against rotation within the recess in said actuator, said snare-rotating shaft having a distally facing manual rotating knob extending beyond the distal face of the actuator and out of the opposite sides of the recess, said rotating knob and the proximal end of the cable each having means cooperating to form a spring biased detent-like connection, said elongated holder, electrically conducting, snare-rotating member and cable defining a common longitudinal axis, and said thumb and finger rings being coplanar with each other and with the holder.

11. In an endoscopic snare having a sheath, an electrically conducting cable with a snare at a distal end movable into and out of the sheath and a manual operating assembly attached to the sheath and to a proximal end of the cable, the improvement wherein the manual operating assembly comprises an elongated holder having a body portion, and a cable actuator, said body portion having a central longitudinal recess open through two opposite sides to define a pair of parallel guides upon which the actuator is slidably mounted, said actuator having an electrically conducting snare-rotating member between said parallel guides, said snare-rotating member and the proximal end of the cable each having means cooperating to form a quick disconnect connection, wherein said elongated holder, snare-rotating member and cable are constructed and arranged to have a common longitudinal axis and wherein said means cooperating to form the quick-disconnect connection comprises a cylindrical transverse rod located near the proximal end of the cable and further comprises an elongated recess transversely centrally located in a distal face of the snare-rotating member, said recess communicating with at least one locking groove, and a spring biased member retained in the shaft of the snare-rotating member and located to releasably engage the rod in the groove.

12. In an endoscopic snare having a sheath, a cable with a snare at a distal end movable into and out of the sheath and a manual operating assembly attached to the sheath and to the proximal end of the cable, the improvement wherein the manual operating assembly comprises a cable actuator having a snare-rotating member, and the proximal end of the cable and said snare-rotating member each have means cooperating to form a quick disconnect connection, wherein said actuator, snare-rotating member, and cable have a common longitudinal axis and wherein the means cooperating to form the quick disconnect connection comprises a transverse rod located near the proximal end of the cable and further comprises an elongated recess transversely centrally located in a distal face of the snare-rotating member, said recess communicating with at least one locking groove, and a spring biased member retained in the shaft of the snare-rotating member located to releasably engage the rod in the groove.

13. The endoscopic snare as claimed in claim 12 wherein said recess communicates with a pair of locking grooves located normal to the elongated recess, and 180° apart from one another.

14. In an endoscopic snare having a sheath, a cable within the sheath, said cable having a snare at a distal end, and a manual operating assembly attached to the sheath and attached to the proximal end of the cable via a cable actuator for moving the distal end of the cable into and out of the sheath, improvement wherein the cable actuator comprises a snare-rotating member, and the proximal end of the cable and said snare-rotating member each have means cooperating to form a quick disconnect connection wholly within said snare-rotating member, said means being constructed and arranged to be accessible for disconnection regardless of the rotational position of the snare rotating member, wherein the means cooperating to form the quick disconnect connection comprises a transverse rod located near the proximal end of the cable, an elliptical recess transversely centrally located in a distal face of the snare-rotating member, said recess communicating with at least one locking groove, a spring biased member retained in the shaft of the snare-rotating member located to releasably engage the rod in the groove, and said manually operating assembly actuator, snare-rotating member, and cable being essentially coplanar.

15. The endoscopic snare as claimed in claim 14 wherein said recess communicates with a pair of locking grooves located normal to the elliptical recess and 180° apart from one another.

* * * * *